United States Patent
Coudane et al.

(10) Patent No.: US 10,603,414 B2
(45) Date of Patent: Mar. 31, 2020

(54) COMPOSITION OF DIBLOCK AND TRIBLOCK COPOLYMERS AND THE USE THEREOF IN THE PREVENTION OF TISSUE ADHESIONS

(71) Applicants: UNIVERSITE DE MONTPELLIER, Montpellier (FR); ECOLE NATIONALE SUPERIEURE DE CHIMIE DE MONTPELLIER, Montpellier (FR); CENTRE NATIONAL DE LA RECHERCHE SCIENTIFIQUE, Paris (FR); CENTRE REGIONAL HOSPITALIER UNIVERITAIRE DE NIMES, Nimes (FR)

(72) Inventors: Jean Coudane, Lattes (FR); Salome Leprince, Saint Laurent de la Salanque (FR); Xavier Garric, Montpellier (FR); Cedric Paniagua, Poussan (FR); Stephanie Huberlant, Montellier (FR); Vincent Letouzey, Nimes (FR)

(73) Assignees: UNIVERSITE DE MONTPELLIER, Montpellier (FR); ECOLE NATIONALE SUPERIEURE DE CHIMIE DE MONTPELLIER, Montpellier (FR); CENTRE NATIONAL DE LA RECHERCHE SCIENTIFIQUE, Paris (FR); CENTRE REGIONAL HOSPITALIER UNIVERSITAIRE DE NIMES, Nimes (FR)

( * ) Notice: Subject to any disclaimer, the term of this patent is extended or adjusted under 35 U.S.C. 154(b) by 0 days.

(21) Appl. No.: 15/502,037

(22) PCT Filed: Aug. 3, 2015

(86) PCT No.: PCT/FR2015/052139
§ 371 (c)(1),
(2) Date: Feb. 6, 2017

(87) PCT Pub. No.: WO2016/020613
PCT Pub. Date: Feb. 11, 2016

(65) Prior Publication Data
US 2017/0224883 A1    Aug. 10, 2017

(30) Foreign Application Priority Data

Aug. 4, 2014 (FR) ...................................... 14 57562

(51) Int. Cl.
*A61L 31/16* (2006.01)
*A61K 31/77* (2006.01)
*A61L 31/14* (2006.01)
*C08G 63/08* (2006.01)
*A61L 31/06* (2006.01)
*C08L 67/02* (2006.01)
*C08G 63/664* (2006.01)
*C08L 67/04* (2006.01)

(52) U.S. Cl.
CPC .............. *A61L 31/16* (2013.01); *A61K 31/77* (2013.01); *A61L 31/06* (2013.01); *A61L 31/148* (2013.01); *C08G 63/08* (2013.01); *C08G 63/664* (2013.01); *C08L 67/025* (2013.01); *C08L 67/04* (2013.01); *A61L 2300/424* (2013.01); *A61L 2300/604* (2013.01)

(58) Field of Classification Search
CPC ... A61K 31/77; A61L 2300/424; A61L 31/06; A61L 31/148; C08G 63/08
See application file for complete search history.

(56) References Cited

U.S. PATENT DOCUMENTS

| 4,716,203 A | 12/1987 | Casey et al. |
|---|---|---|
| 7,202,281 B2 | 4/2007 | Cohn et al. |
| 2013/0338762 A1 | 12/2013 | Jayasinghe et al. |

FOREIGN PATENT DOCUMENTS

| EP | 1 642 921 A1 | | 4/2006 | |
|---|---|---|---|---|
| WO | WO 98/02171 | * | 7/1997 | ........... A61K 31/765 |
| WO | 98/02171 A1 | | 1/1998 | |
| WO | WO 98/02171 | * | 1/1998 | ........... A61K 31/765 |

OTHER PUBLICATIONS

Yang et al.: "Tissue anti-adhesion potential of biodegradable PELA electrospun membranes", Acta Biomaterialia, Elsevier, Amesterdam NL, vol. 5, No. 7, Sep. 1, 2009, pp. 2467-2474, SP026500010, retrieved on Apr. 1, 2009.
International Search Report, dated Nov. 6, 2015, from corresponding PCT application.

* cited by examiner

*Primary Examiner* — Anna R Falkowitz
(74) *Attorney, Agent, or Firm* — Young & Thompson

(57) ABSTRACT

Disclosed is a composition based on copolymers including at least one A-B block copolymer, wherein block A is a polyester and block B is a polyoxyethylene (PEG), and wherein the total molecular mass in weight of the PEG is higher than or equal to 50 kDa, and the ethylene oxide motif/ester motif molar ratio is between 0.5 and 5. The invention also relates to an anti-adhesive material including such a composition, used for the prevention of tissue adhesions and especially for the prevention of intrauterine synechiae.

18 Claims, 10 Drawing Sheets
(7 of 10 Drawing Sheet(s) Filed in Color)

FIGURE 8 (continue)

COMPOSITION OF DIBLOCK AND TRIBLOCK COPOLYMERS AND THE USE THEREOF IN THE PREVENTION OF TISSUE ADHESIONS

The invention relates to a novel composition of diblock and/or triblock copolymers based on polyester and polyoxyethylene blocks, and to the use thereof for the manufacture of an anti-adhesion material particularly suited to the prevention of tissue adhesions and more particularly intrauterine adhesions or synechiae.

TECHNOLOGICAL BACKGROUND

Intrauterine synechiae or adhesions, also known, in the most severe cases, as Asherman's syndrome, consist of partial or total adhesion of the cervical and/or uterine body walls. They are often accompanied by chronic abdominal pain and dysmenorrhea, and may lead to mechanical infertility due to implantation failure. It is acknowledged today that intrauterine synechiae are most often due to a surgical procedure performed in the uterine cavity, such as Cesarean section, endometrial resection, curettage subsequent to childbirth or miscarriage, etc.

Once diagnosed, intrauterine synechiae are generally treated by operative hysteroscopy, using micro scissors introduced into the uterine cavity to section the fibrous synechia bridges. The synechia reformation rate remains, however, relatively high, and may even reach more than 40% in cases of severe synechiae.

Currently, there is little or no progress in preventing synechiae. A solution may consist in placing a physical barrier in the uterine cavity of patients at risk, in order to prevent tissue adhesion. However, the products developed to date are unsatisfactory.

Thus, gels based on hyaluronic acid and/or polyethylene glycol have been developed (Hyalobarrier® from Nordic Pharma, SprayShield® from Covidien), to be deposited on the uterine wall after a surgical procedure. However, particularly due to their galenic gel form, these products are eliminated very rapidly, and have a residence time in the uterus lower on average than 24 hours. However, it is known that synechiae develop within 1 to 8 days after the occurrence of uterine trauma. The too-rapid elimination of these gels thus prevents them from acting satisfactorily to prevent the formation of fibrous synechia bridges.

A film composed of synthetic hyaluronic acid, associated with a carboxymethyl cellulose/glycerol substrate, has also been developed (Seprafilm® from Genzyme). If this type of film is commonly used to prevent postoperative adhesions in abdominal surgery, it is not satisfactory for intrauterine synechiae. Indeed, the morphology and the mechanical properties of the film make it difficult or impossible to introduce it into the uterine cavity via the cervix.

Also known from the document U.S. Pat. No. 7,202,281 is a composition comprising copolymers based on polylactic acid (PLA) and polyethylene glycol (PEG) having a molecular weight of 6,000, used to form an anti-adhesion film for preventing synechiae particularly in the abdominal region. Such a film is however not satisfactory in the context of preventing intrauterine synechiae.

There is thus a genuine need for a product that can be easily positioned in the uterine cavity and whose physical and chemical properties make it possible to prevent the formation of synechiae, particularly in patients having undergone a surgical procedure in the uterine cavity.

SUMMARY OF THE INVENTION

In this context, the inventors discovered that the use of copolymers based on polyester blocks, such as poly-lactic acid (PLA), and high molecular weight polyethylene glycol (PEG) blocks, makes it possible to produce a material combining properties of surface anti-adhesion, of swelling and of resorption particularly suited to use in the uterine cavity for preventing the formation of synechiae therein. The inventors thus developed a medical device from such a material, which in "dry" form has dimensions allowing easy placement via the cervix, and which once in the uterine cavity dampens and deploys to mold itself to the contours of the uterine cavity. Indeed, the material according to the invention has a swelling ratio in aqueous medium that enables it to increase its volume up to about ten times compared to the "dry" form. Moreover, the disintegration time of this material is generally between 5 and 20 days, which makes it possible not only to guarantee a sufficient residence time of the medical device in the uterine cavity in order to prevent the formation of fibrous synechia bridges, but also to ensure its elimination naturally, in particular during the following menstrual cycle.

The invention thus relates to a composition based on copolymers comprising at least one copolymer block A and B, wherein:
- the A block is a polyester,
- the B block is a poly-oxyethylene (PEG),
- the molecular mass in weight of the B blocks is 50 kDa or greater, and
- the ethylene oxide unit/ester unit molar ratio is 0.5 to 5.

Advantageously, the molecular mass of the B blocks in the copolymer is between about 50 kDa and about 300 kDa. In a particular embodiment, the molecular mass of the PEG is between about 75 kDa and about 150 kDa, preferably between about 80 and about 125 kDa, more preferably between about 90 and about 115 kDa, even more preferably between about 100 kDa and about 110 kDa.

Preferably, the composition according to the invention is composed only of A and B block copolymers. In a particular embodiment, the composition comprises ABA triblock copolymers. In another embodiment, the composition is composed only of ABA triblock copolymers.

The invention also relates to an anti-adhesion material obtained by forming such a copolymer-based composition. The material according to the invention is particularly suited to medical use especially for preventing tissue adhesions, and more specifically for preventing intrauterine synechiae. The material can in particular have the form of a film or a tube.

The invention also relates to a medical device for preventing intrauterine synechiae comprising said anti-adhesion material. Advantageously, the medical device further comprises means for inserting said material able to introduce and release said material in the uterine cavity of a patient.

Likewise, the invention relates to the use of such a composition, such a material, and/or such a medical device for preventing tissue adhesions, and particularly intrauterine synechiae in patients at risk. For example, the material according to the invention can be used systematically in patients having just undergone Cesarean section, abortion or any intrauterine surgical procedure able to cause synechiae, such as bilateral resection of fibroids, in particular by myomectomy.

The invention also relates to a method for preventing intrauterine synechiae in a patient at risk, according to which one introduces into the uterine cavity of said patient an anti-adhesion material produced from a composition based on copolymers comprising at least one A and B block copolymer, wherein the A block is a polyester,
the B block is a poly-oxyethylene (PEG),
the molecular mass of the B blocks is 50 kDa or greater, and
the ethylene oxide unit/ester unit molar ratio is 0.5 to 5.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 1b presents the comparative results obtained during a cell adhesion test carried out on two materials according to the invention, namely copolymer P4 and PLA-PEG 95 kDa-PLA triblock copolymer with an EO/LA molar ratio of 1 (hereafter copolymer P3), and on a commercial anti-adhesion material, Seprafilm, and two controls (TCPS and $PLA_{50}$). The fluorescence values (AU 615 nm) reflect the quantity of cells having adhered on the film at t=45 minutes, t=1.5 hours and t=3 hours. The cells used are human endometrial cells (FIG. 1b);

FIG. 4a shows the percentage of water uptake of said materials over time, FIG. 4b shows the corresponding percentage of increase in surface area, and FIG. 4c shows the corresponding percentage of increase in volume;

FIG. 8a shows the elastic modulus G' and the viscous modulus G" of the copolymer P3 and P4 films after 5 minutes of immersion, when a fixed-frequency (1 Hz) deformation range is applied thereto. FIG. 8b shows the variation of the elastic modulus (G') and of the viscous modulus (G") as a function of frequency (at 0.05% deformation) for copolymers P4 and P3 after 2 days and 21 days of immersion. FIG. 8c shows the elastic modulus (G') at various incubation times for copolymers P4 and P3. FIG. 8d shows the stress of copolymer P4 after 30 days of incubation and the stress of copolymer P3 after 40 days of incubation as a function of shear rate;

FIG. 13a shows the adhesion of the cecum and the peritoneum 12 days after the surgery with no anti-adhesion treatment or agent being applied (control rat). FIG. 13b shows the condition of the adhesion-free abdominal cavity 12 days after the surgery with the application of a film produced according to the invention based on copolymer P4. FIG. 13c shows the condition of the adhesion-free abdominal cavity 12 days after the surgery with the application of a film produced according to the invention based on copolymer P3;

DETAILED DESCRIPTION

Figure 1:
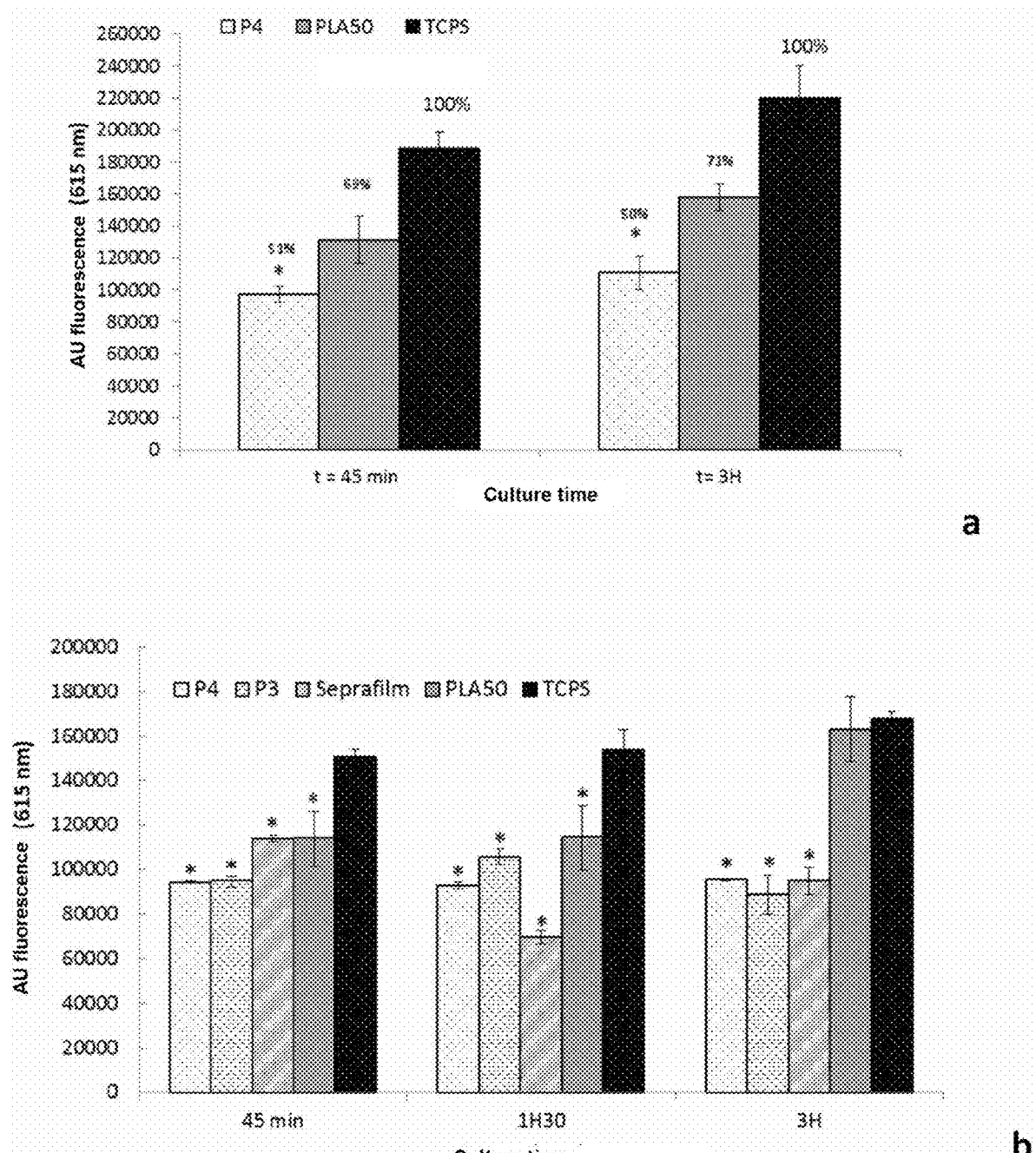
FIG. 1 shows the results obtained during a cell adhesion test carried out on a material according to the invention comprising PLA-PEG 95 kDa-PLA triblock copolymers, with an ethylene oxide/lactic acid (EO/LA) molar ratio of 3 (hereafter copolymer P4) and on two controls (TCPS and $PLA_{50}$). The fluorescence values (AU 615 nm) reflect the quantity of cells having adhered on the film at t=45 minutes and t=3 hours. The cells used are murine fibroblast lines (L929) commonly used for in vitro evaluation of medical devices (FIG. 1a).

The inventors developed a composition comprising block copolymers based on polyester blocks and high molecular weight poly-oxyethylene (PEG) blocks having mechanical and chemical properties particularly suited to use in the medical field, and especially to the prevention of intrauterine synechiae. Indeed, the swelling and deployment properties of the composition, combined with its properties of anti-adhesion and of degradation in a few days, make it is possible to use it temporarily in the intrauterine cavity to reliably prevent adhesions of the uterine walls.

Composition

The present invention relates to a composition based on copolymers comprising at least one A and B block copolymer, where A is a polyester and B is poly-oxyethylene (PEG), and wherein the molecular mass of the B blocks in the copolymer is 50 kDa or greater and the ethylene oxide unit/ester unit molar ratio is between 0.5 and 5.

In the context of the invention, the expression "between x and y" means that the values x and y are included.

According to the invention, the term "polyester" refers to any polymer whose repeat units of the main chain contain the ester function and which can be used in the medical field. In particular, "polyesters" means aliphatic polyesters such as poly(lactic acid) (PLA), poly(glycolic acid), poly-caprolactone (PCL), poly-butyrolactone (PBL), poly-hydroxyalkanoates (PHA), and copolymers thereof.

In a preferred embodiment, the polyester (A block) is selected from poly(lactic acid) (PLA), poly(glycolic acid), poly-caprolactone (PCL) and copolymers thereof.

Preferably, the polyester present in the composition is in a non-crosslinked form.

The poly(lactic acid) can be poly(L-lactic acid), poly(D-lactic acid) or poly(D,L-lactic acid). Advantageously, poly(D,L-lactic acid) (PDLLA) is used. In this case, the polymer comprises preferably at least 50% L-lactic acid, and in particular at least 60%, 70%, 75%, 80%, 85%, 90%, 95% or 99%. Indeed, by modifying the percentage of L-lactic acid in relation to D-lactic acid, it is possible to adjust the degradation rate of the A and B block copolymer. An increase in the L-lactic acid level makes it possible to slow down the degradation rate of the copolymer. In certain embodiments of the invention, the composition comprises 100% PLLA as the A blocks.

According to the invention, the PEG used has a high molecular weight, so that the total molecular weight of the PEG in the copolymer is 50 kDa or greater. Indeed, the inventors discovered that a copolymer wherein the PEG has a molecular weight of 50 kDa or greater, preferably greater than 75 kDa, and more preferably 100 kDa or greater, makes it possible to confer upon the composition particularly advantageous film-forming properties in the context of medical use in the form of an anti-adhesion film or membrane. By "film-forming properties" is meant that the composition is able to form a homogeneous and continuous film. More particularly, these film-forming properties make the composition particularly stable and homogeneous over time and lead to the formation of a film having good performance in aqueous medium.

In the context of the invention, the terms "molecular mass" and "molecular weight" are used interchangeably to indicate, unless otherwise stated, the weight average molecular weight (Mw). According to the invention, Mw is determined by size-exclusion chromatography carried out in dimethylformamide as the analysis solvent, using a standard range of poly(ethylene glycol).

Advantageously, the total molecular mass of the PEG in the copolymer is between about 50 and about 300 kDa. For example, the PEG blocks have a molecular mass of about 50 kDa, 75 kDa, 100 kDa, 125 kDa, 150 kDa, 200 kDa, 225 kDa, 250 kDa, 275 kDa or 300 kDa. In a particular embodiment, the PEG blocks used have a molecular mass between about 75 kDa and about 150 kDa, preferably between about 80 and about 125 kDa, more preferably between about 90 and about 115 kDa, even more preferably between about 100 kDa and about 110 kDa. In a particular embodiment, the PEG blocks used have a molecular mass between 95 and 105 kDa.

According to the invention, the PEG blocks used advantageously have an inherent viscosity between 0.04 mg/ml and 0.6 mg/ml, preferably between 0.08 mg/ml and 0.5 mg/ml, and even more preferably between 0.1 mg/ml and 0.3 mg/ml when measured by an Ubbelohde-type capillary viscometer at a concentration of 1 g/l, at 25° C. in chloroform.

Advantageously, the composition based on copolymers according to the invention comprises AB diblock, or ABA or BAB triblock copolymers, or mixtures thereof, in particular [ABA and BAB], [AB and ABA], [AB and BAB], [ABA and BAB and AB]. Preferably, the composition comprises only A and B block copolymers. In a particular embodiment, the composition according to the invention comprises only ABA or BAB triblock copolymers, and preferably only ABA triblock copolymers. According to the invention, in a composition of AB and/or ABA copolymers each PEG block has a molecular mass of 50 kDa or greater and advantageously between about 50 and about 300 kDa, preferably between about 75 kDa and about 150 kDa, preferably between about 80 and about 125 kDa, more preferably between about 90 and about 115 kDa, even more preferably between about 100 kDa and about 110 kDa, or between 95 and 105 kDa, whereas in a composition comprising BAB copolymers, the sum of the molecular masses of the PEG blocks in said copolymer is 50 kDa or greater and advantageously is between about 50 and about 300 kDa, preferably between about 75 kDa and about 150 kDa, preferably between about 80 and about 125 kDa, more preferably between about 90 and about 115 kDa, even more preferably between about 100 kDa and about 110 kDa, indeed between 95 and 105 kDa.

In the context of the invention, molar ratio represents the molar ratio of each repeat unit of the A and B blocks. The B block being PEG, the repeat units are ethylene oxides ("ethylene oxide unit" or EO), whereas the repeat units of the A block ("ester unit") are carboxylic acids such as lactic acid units. According to the invention, the EO/ester unit molar ratio in the copolymers of the composition is between 0.5 and 5, and preferably between about 1 and 3. The molar ratio is measured from the proton nuclear magnetic resonance (NMR) spectrum in deuterated chloroform of the copolymer in which it is possible to identify the chemical shifts of the peaks characteristic of PLA-PEG-PLA: CH (PLA): 5.1 ppm; $CH_2$(PEG): 3.5 ppm; $CH_3$(PLA): 1.5 ppm copolymers). The compositions whose copolymers have an EO/ester unit molar ratio, and particularly an ethylene oxide unit/lactic acid unit (EO/LA) molar ratio, between about 1 and 3 have swelling and deployment properties such that the volume increases up to ten times in aqueous medium, which makes these compositions particularly suited to medical use for preventing intrauterine synechiae. It is noted that the compositions having an EO/LA molar ratio of about 3 degrade within a shorter amount of time, about 3 to 5 days, in an aqueous medium such as phosphate-buffered saline (PBS), than the compositions comprising an EO/LA molar ratio of about 1, which degrade within about 5 to 20 days.

In the context of the invention, the term "about" means the given value plus or minus 10%.

According to the invention, a "aqueous medium" refers to a medium having a osmolarity similar to the osmolarity of biological fluids. Phosphate-buffered saline (PBS), regarded as representative of biological fluids, is commonly used as an aqueous medium.

In a particular embodiment, the composition consists of ABA triblock copolymers, where the A block is PDLLA and the B block is PEG having a molecular weight of about 100 kDa, wherein the EO/LA molar ratio is equal to about 1.

In another particular embodiment, the composition consists of ABA triblock copolymers, where the A block is PDLLA and the B block is PEG having a molecular weight of 100 kDa, wherein the EO/LA molar ratio is equal to about 3.

The composition according to the invention can be obtained by any block copolymer synthesis method known the person skilled in the art. For example, an ABA-type copolymer can be obtained by chain polymerization from the ends of the B block. Typically, polymerization is carried out by opening the lactide ring primed by the terminal hydroxyls of the PEG block in the presence of a catalyst such as tin octanoate. This polymerization can be carried out in the absence or in the presence of solvents. A BAB-type copolymer can be prepared for example by coupling of methoxy-PEG on a PLA chain whose two chain ends are carboxylic acid functions. Such a "difunctionalized" PLA is obtained for example by treating a PLA chain with succinic or adipic anhydride.

In a particular embodiment, the composition according to the invention comprises A and B block copolymers, where the B blocks (high molecular weight PEG) are obtained from several PEGs of lower molecular weights. For example, the composition comprises 100 kDa PEG produced with shorter PEG blocks (for example between 5 and 25 kDa), joined together by degradable bonds. During the degradation of the copolymers, the 100 kDa PEG blocks then degrade into 5 to 25 kDa subunits, which can pass through glomerular filtration and thus be eliminated in the urine. This embodiment is particularly advantageous when it is desired to use the composition according to the invention for preventing tissue adhesions other than intrauterine synechiae.

Anti-Adhesion Material

The invention also relates to an anti-adhesion material obtained by forming the composition based on A and B block copolymers described above.

The forming of the material can be done by any means known to the person skilled in the art, and particularly by extrusion, solvent evaporation using for example dichloromethane, hot pressing, molding or 3D printing.

Generally, the thickness of the material obtained depends on the quantity of the composition used and the surface area of the substrate or the mold used for the forming process.

The material according to the invention can thus take the form of a film, a tube, a porous structure, such as a 2D or 3D matrix of gel or porous hydrogel, etc.

A "film" means a two-dimensional material, resulting from the evaporation on a planar surface of the solvent having dissolved the copolymer of the composition according to the invention. The thickness of such a film is advantageously between a few microns and several hundred microns, and particularly between 10 µm and 500 µm. In a particular embodiment, the film has a thickness between about 100 µm and 300 µm. "Thickness" means "dry", in the sense that it is measured (for example by light microscopy) in anhydrous conditions, after forming and total evaporation of the solvent having served to dissolve the copolymer.

The dimensions of the film can be adapted according to needs, in particular by cutting a film of greater dimensions to the desired dimensions.

The films can be folded to form tubes, or sleeves, held closed as needed by suturing or gluing. Tubes can also be obtained directly by forming around a cylinder or by extrusion.

In the context of the invention, a "tube" refers to a hollow three-dimensional cylindrical object whose walls are formed of a copolymer film comprising at least one A and B block copolymer according to the invention. Preferably, the diameter of such a tube is several hundred microns, and in particular between 300 µm and 3,000 µm. In a particular embodiment, the tube has a wall thickness of about 300 µm and a diameter of about 900 µm.

In a particular embodiment, the material is obtained by forming the composition on a substrate intended to form part of said material. For example, the composition is dried on a woven or knitted textile consisting of another polymer, the whole thus forming a mixed material.

Advantageously, the material comprises only the components of the composition based on copolymers according to the invention, and optionally traces of solvent. For example, the material comprises only copolymers of PLA and high molecular weight (50 kDa or greater) PEG. In a particular example, the material comprises only copolymers of PLA and PEG, wherein the PEG has a molecular weight of about 100 kDa.

In certain cases, the material can comprise, in addition to the components of the composition according to the invention, an additional additive or active ingredient, such as an anti-adhesion molecule or a therapeutic molecule such as an antibiotic. This additive or active ingredient can for example be added to the copolymer-based composition before or during the forming of the material, so as to be dispersed in the polymeric matrix of the material. Otherwise, it is possible to impregnate or cover the material with this active ingredient after the forming process. Preferably, the active ingredient is able to diffuse toward the outside of the material when it is in an aqueous medium.

The material according to the invention has anti-adhesion, resorption and swelling properties particularly suited to medical use for preventing tissue adhesions and particularly intrauterine synechiae.

By "anti-adhesion properties" is meant that the material according to the invention is able to prevent or at the very least to limit cell proliferation and cell adhesion on its surface, compared to a material not having such properties. The anti-adhesion properties can be measured by evaluating over time, on the surface of the material, the cell adhesion rate by measuring fluorescence reflecting the quantity of cells having adhered to the surface of the material. Similarly, the cell proliferation rate can also be evaluated by measuring fluorescence on the surface of the material.

The use of high molecular weight PEG in the composition used to form the material makes it possible to confer upon same particularly advantageous anti-adhesion properties in the context of preventing synechiae, and particularly intrauterine synechiae. Thus, a material obtained by forming a composition based on ABA triblock copolymers where A is PDLLA and B is 100,000 PEG (i.e., a molecular weight of about 100 kDa), and whose EO/LA molar ratio is about 1 or about 3, has a cell adhesion rate 2 times lower than the rate obtained with the adhesion films of the state of the art.

Advantageously, the material according to the invention has, in an aqueous medium having an osmotic pressure identical to that of biological fluids, a swelling ratio between about 1 and 20, and preferably between about 3 and 15. Preferably, the material according to the invention has a swelling ratio at least equal to 4. The swelling ratio is measured in the following manner: a strip of dry material is weighed before being immersed for 24 hours at 37° C. in saline medium (1×PBS) with shaking. After 24 hours, the excess PBS is removed with absorbent paper and the strip is weighed again. The swelling ratio corresponds to the following ratio: mass of the strip of wet material/mass of the strip of dry material. The swelling ratio of the material is proportional to its percentage of water uptake, which corresponds to the ratio [(mass of the strip of wet material−mass of the strip of dry material)/mass of the strip of dry material]×100.

The swelling of the material is accompanied by an increase in surface area and in volume ("hydrated" surface area or volume), which is particularly advantageous during medical use for preventing intrauterine synechiae, since that promotes the deployment of the material in the uterine cavity, particularly in order to mold to its contours.

The increase in surface area is very fast and can in particular reach 200 to 300% in the space of a few minutes to a few hours in aqueous medium. A plateau around 300 to 400% is advantageously observed after 4 to 5 hours in aqueous medium. The increase in surface area is accompanied by an increase in the volume of the material, which is measured visually, under the same conditions as during the measurement of the swelling ratio, by modifying only the residence times in the saline solution. The increase in surface area corresponds to the ratio [(surface area of the "hydrated" strip after an immersion time t−surface of the "dry" strip)/surface of the "dry" strip]×100.

A particularly advantageous additional feature of the material according to the invention is that it does not degrade quickly in aqueous medium, permitting a residence time in the uterine cavity between 1 and 40 days, preferably between 2 and 20 days, and more preferably between 3 and 15 days, while retaining its integrity for a period of at least between 1 and 15 days. The degradation of the material is due to the progressive hydrolysis of the ester bonds of the polyester blocks followed by solubilization of the blocks containing PEG. The loss of the mechanical properties of the material is directly related to its degradation. The degradation can be evaluated by measuring over time the decrease in the molecular weight of a strip of material, after immersion at 37° C. in saline medium (1×PBS) with shaking, for example by size-exclusion chromatography. It is also possible to evaluate the decrease in the dynamic viscosity of the material. A loss of viscosity of about 30 to 50% is generally observed after 7 days of immersion at 37° C. in saline medium (1×PBS) with shaking, and up to 70% after 15 days.

A modification of the mechanical properties of the material according to the invention is also observed in vivo. More precisely, it passes from the film state to the gel state in a few days. In particular, with an ABA triblock copolymer wherein A is PLA and B is PEG having a molecular mass of about 100 kDa, passage from the film state to the gel state occurs after 2 days when the EO/LA ratio is 3, and after 12 days when the EO/LA ratio is 1. These modifications of the mechanical properties are directly related to hydrolytic degradation.

Thus, the composition according to the invention exhibits a balance between the swelling ratio of the polymers and the degradation rate thereof, which makes it possible to guarantee that the material obtained from such a composition has a residence time in the uterine cavity of a sufficient period, advantageously between about 3 and 15 days, during which the mechanical properties and the physical integrity of said material are at least partially preserved. In particular, the anti-adhesion properties and the "hydrated" volume of the material endure for a sufficient time to prevent the formation of synechiae when said material is placed in the uterine cavity of a patient after a trauma of the uterine wall. The solubilization of the PEG blocks and the hydrolysis of the polyester blocks in the uterine cavity are progressive, and are generally sufficient after 10 to 15 days to allow the elimination of the material, in particular during menstruation which generally follows the placement of said material in the uterine cavity.

Medical Device and Use

The invention also relates to a medical device for preventing intrauterine synechiae comprising the anti-adhesion material according to the invention.

In a particular embodiment, the medical device comprises a film or a tube obtained by forming a composition consisting of ABA triblock copolymers where A is PDLLA and B is PEG having a molecular weight of about 100 kDa, wherein the EO/LA ratio is about 1.

In another embodiment, the medical device comprises a film or a tube obtained by forming a composition consisting of ABA triblock copolymers where A is PDLLA and B is PEG having a molecular weight of about 100 kDa, wherein the EO/LA ratio is about 3.

Advantageously, the medical device comprises a film of material according to the invention having the shape of a triangle or a trapezoid, in order to best mold, once hydrated and deployed by swelling, to the inner contours of the uterine cavity in which it is intended to be placed.

The film can for example have a dry thickness of about 300 to 500 microns.

Figure 14:
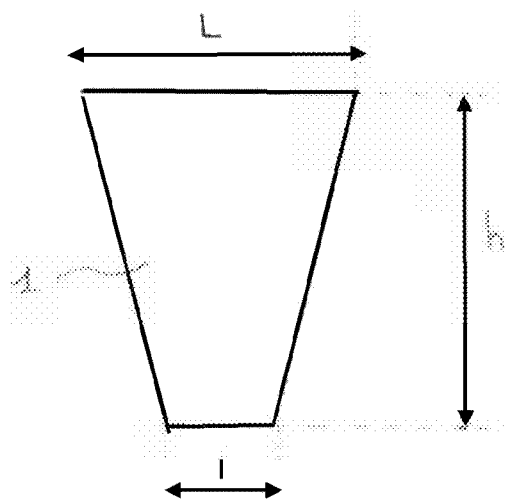
FIG. 14 is a schematic representation of an anti-adhesion film according to the invention in the shape of a trapezoid, particularly suited to use in a human uterine cavity, as it is able to mold to the contours thereof after swelling and deployment.

In a particular embodiment, as represented in FIG. 14, the film 1 has a trapezoidal shape having a height h between about 1 and 2 cm, a greatest width L between about 1 and 1.5 cm, and a smallest width l between about 0.25 and 0.75 cm. For example, the trapezoid has a height of about 1.5 cm, a greatest width L of about 1.25 cm and a smallest width l of about 0.5 cm. These dimensions are easily adaptable by the person skilled in the art, in particular in the ranges above, according to the type of patient to be treated, according to whether she is primiparous or multiparous, her age, the reasons for concern about the occurrence of synechiae, etc.

The device according to the invention advantageously comprises means for inserting and placing the material in the uterine cavity.

Figure 15:
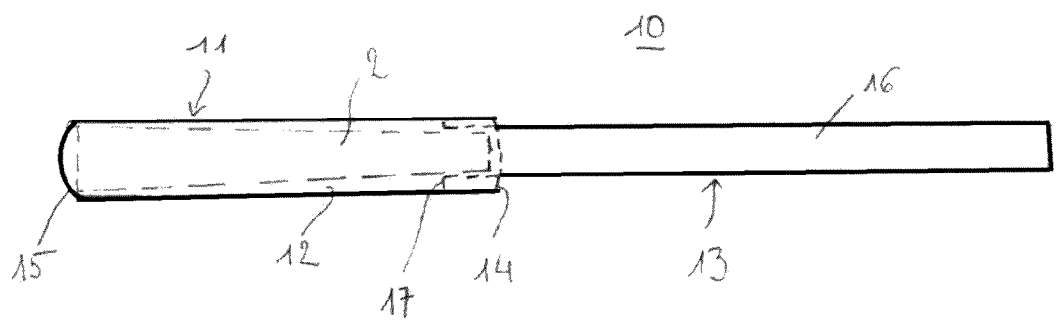
FIG. 15 is a longitudinal cross-section of a schematic representation of an example embodiment of the medical device according to the invention comprising means for inserting the anti-adhesion material in a uterine cavity.

For example, as represented in FIG. 15, the device 10 according to the invention comprises a hollow cylindrical inserter 11, in the bore 12 of which a film 2 having an inverted trapezoidal shape is placed. Advantageously, in order to maximally reduce the dimensions of the inserter 11, the film is placed in the bore 12 in a compacted form. For example, the film is folded into an accordion shape and held tight by the inner walls of the bore 12. It is only once released in the uterine cavity that the accordion is deployed. This deployment is further promoted by the near-concomitant increase in the volume of the film, the polymers of which swell with water in contact with the intrauterine fluid.

The medical device 10 advantageously comprises a plunger 13 mounted to be slidable in translation relative to a distal end 14 of the inserter, the opposite proximal end 15 being the end by which the inserter 11 is intended to be introduced into the uterine cavity. The plunger 13 consists of a shaft 16 which, when it is pushed inside the bore 12 of the inserter 11, toward the proximal end 15, leads the film 2 in translational motion toward the outside of the inserter 11.

Advantageously, the plunger 13 comprises stopping means 17 at the proximal end of the shaft 16, said stopping means 17 being designed to abut the wall of the bore 11 bordering the proximal end 15 of the inserter, in order to inform the person handling the device 10 that the film 2 has been fully ejected from the inserter and that it is in position in the uterine cavity. It then suffices to withdraw the entire insertion means/inserter by simply pulling toward the outside, the film 2 remaining in position in the uterine cavity.

Such a system makes it possible to introduce and to place in a reliable manner the anti-adhesion material according to the invention. Furthermore, this compacted form makes it possible to further reduce the dimensions of the material before swelling, which facilitates its introduction via the patient's cervix.

The medical device according to the invention can advantageously be used systematically in patients having just undergone Cesarean section, or any other surgical procedure of the abdominopelvic cavity. The compacted form of the anti-adhesion material and the employment of an applicator of small dimensions facilitate its placement in the often-sensitive uterine cavity of these patients. Moreover, its natural elimination during the menstrual cycle makes it possible for patients to avoid an additional procedure by medical staff in order to remove said device.

The invention will now be illustrated using the examples below, which are presented for purposes of illustration and which in no way limit the invention.

Examples

1—Synthesis of ABA Triblock Polymers

Material

Commercial poly(ethylene-oxide) (PEG): Supplier Aldrich Sigma, CAS no. 25322-68-3. The commercial PEG was analyzed in the laboratory at the size-exclusion chromatography (SEC) in order to determine its weight average molar mass (Mw). The analysis was carried out in an analysis solvent (dimethylformamide), and the Mw was determined via a standard range of poly(ethylene glycol).

The weight average molar mass (Mw) is 95,000 Da and its inherent viscosity is 0.16 ml/mg.

The lactide used in the composition can be D,L-lactide, D-lactide, D-lactide or the combination of D-lactide and D-lactide. The proportions of lactide introduced during the synthesis depend on the percentage of L- or D-lactide desired in the composition of the final polymer.

Method

The ABA triblock is synthesized as follows:

The PEG (Mw 95,000) and the lactide are dried under vacuum at room temperature for 24 h. The PEG and the lactide (the quantity of lactide depends on the desired length of the A block) are introduced into a round-bottom polymerization flask in the presence of tin octanoate. Ten successive cycles of vacuum ($10^{-3}$ bar) and of argon are then carried out. The mixture is then heated to 140° C. and 10 successive cycles of vacuum and of argon are repeated. The mixture is returned to room temperature, then placed in an ice bath. Once crystallized, the reaction mixture is placed under dynamic vacuum for 30 min, then sealed under dynamic vacuum. The mixture is then placed in a 140° C. heat chamber with mechanical rotation for 3 days. The mixture is dissolved in dichloromethane and precipitated in an ether/ethanol mixture. The precipitate is collected then dried under vacuum for 24 h.

Characterization

One of the ABA triblocks presented in this report is obtained from PEG (Mw 95,000 Da) and from D,L-lactide. The final composition of the copolymer, called copolymer P4, was determined by proton nuclear magnetic resonance ($^1$H NMR) and an EO/LA molar ratio of 3 was deduced therefrom.

Two-dimensional NMR analysis (DOSY) indicates that the synthesis produced an ABA triblock.

The copolymer was also analyzed by size-exclusion chromatography (SEC) in order to determine its average molar mass (Mw) and its dispersity ($I_p$).

With an analysis solvent such as dimethylformamide and using a standard range of poly(ethylene glycol), a Mw of 123,000 Da and a dispersity close to 5 are obtained.

Moreover, thermogravimetric analysis (TGA) made it possible to determine the degradation temperature of copolymer P4, which is 256° C.

2—Forming the Anti-Adhesion Material

The forming of an anti-adhesion film from the composition of triblock copolymers is carried out as follows:

A. By solvent evaporation: the copolymer is dissolved in dichloromethane (50 mg/ml). The solution is deposited on a substrate and the dichloromethane slowly evaporates to form a film. The thickness of the film depends on the volume of the solution of dissolved copolymers used and on the surface area of the substrate.

B. By hot pressing: the copolymer is heated to 100° C. for 10 min then placed between two heating plates. Pressure (3,000 psi) is then applied between the two plates. The thickness of the film depends on the quantity of copolymer used and the surface area of the substrate.

C. By three-dimensional printing using fused deposition modeling (FDM) technology: the copolymer is first extruded (T°=120° C.) to form a homogeneous filament. The copolymer filament is then used to print the 3D-modeled object.

Generally, P3 film, P4 film and PLA$_{50}$ film refer to films produced from compositions of copolymers P3, P4 and PLA$_{50}$, respectively.

3—Evaluation of Anti-Adhesion Properties and Biocompatibility of the Anti-Adhesion Material The objective of this study is to show the anti-adhesion effect and the absence of cytotoxicity. For all the tests carried out in cell culture, the copolymers have as a composition:

ABA triblock obtained from PEG (Mw 95,000) and D,L-lactide. The final EO/LA molar ratio is 3 (determined by proton nuclear magnetic resonance ($^1$H NMR)). The polymer is called copolymer "P4".

Forming a film of copolymer P4 (hereafter P4 film): by solvent evaporation. Thickness of 300 μm (measurement obtained with a light microscope).

ABA triblock obtained from PEG (Mw 95,000) and D,L-lactide. The final EO/LA molar ratio is 1 (determined by proton nuclear magnetic resonance ($^1$H NMR)). The copolymer is called copolymer "P3".

Forming a film of copolymer P3 (hereafter P3 film): by solvent evaporation. Thickness of 300 μm (measurement obtained with a light microscope).

The controls used are selected from the following controls
Positive control: TCPS (wells);
Negative control: TCPS (wells) with addition of cell lysis solution. The whole induces a reproducible cytotoxic response;
PLA$_{50}$, known as a biocompatible material which promotes cell proliferation. Forming identical to the P4 and/or P3 evaluated;
Seprafilm (Genzyme S.A.S), commercial anti-adhesion barrier consisting of hyaluronic acid and carboxymethylcellulose.

The cells used are a CCL 1 murine dermal fibroblast line (NCTC clone 929), recommended for evaluating the in vitro cytocompatibility of medical devices according to the EN ISO 10993-5 standard, or a human endometrial cell culture.

All the tests are carried out in triplicate to ensure the reproducibility of the results.

A. Cell Adhesion Test

The PrestoBlue® test makes it possible to evaluate cell viability by measuring the metabolic activity of cells. The test (Student's t-test) is carried out after direct contacting of the cells on the material in order to quantify the adherent cells.

The fluorescence values corresponding to the quantity of adherent cells are measured by fluorescence spectrophotometry (λ Excitation=531 nm; λ Emission=615 nm).

The P4 film used is first immersed in pH 7.4 PBS for 24 h in order to swell.

As seen in FIG. 1a, the fluorescence values reflect the quantity of cells having adhered on the film. A significant decrease in cell adhesion on the P4 film in comparison with the PLA$_{50}$ film and the TCPS positive control is observed.

Thus, by considering that 100% of the cells adhere on the positive control (TCPS), 69% of the cells adhere on the PLA$_{50}$ film and only 51% of the cells adhere on the P4 film after 45 minutes of incubation. The percentages are similar after 3 hours of incubation.

FIG. 1b confirms the reduction in cell adhesion on the P4 films and the P3 films. A reduction in the adhesion of human endometrial cells is observed on the P4 and P3 films in comparison with the TCPS positive control after 45 minutes, 1.5 hours and 3 hours of incubation. Equivalent cell adhesion is also observed on the P4 films, the P3 films and the Seprafilm® anti-adhesion membrane after 3 h of incubation.

B. Cell Proliferation Test

The P4 and P3 films used are first immersed in pH 7.4 PBS for 24 h in order to swell.

Figure 2:
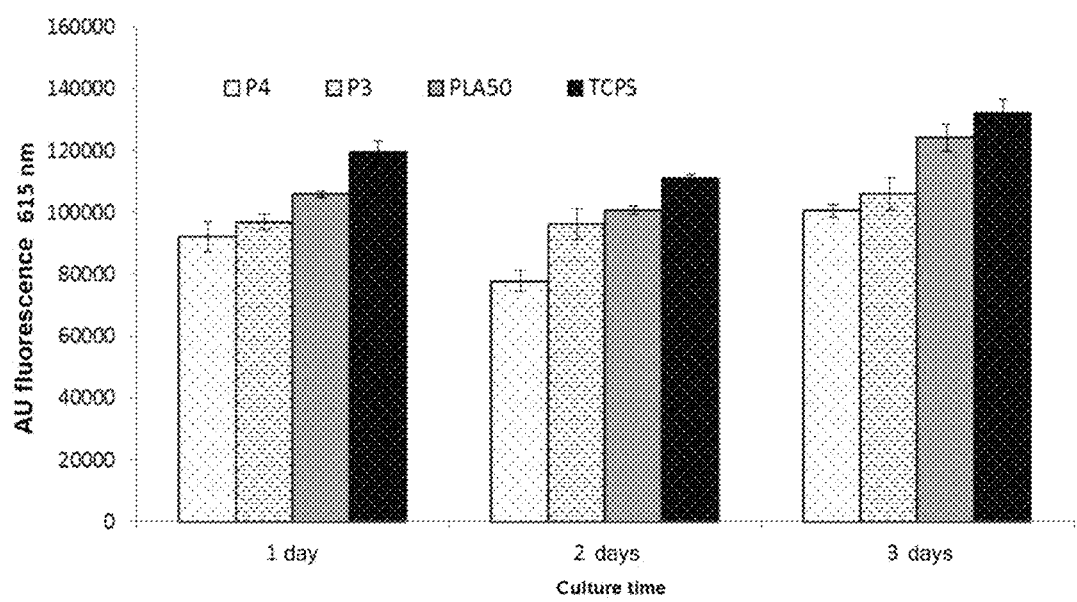
FIG. 2 shows the results obtained during a cell proliferation test carried out on a material according to the invention produced from copolymer P4, and on a second material according to the invention comprising PLA-PEG 95 kDa-PLA triblock copolymers, with an EO/LA molar ratio of 1 (hereafter copolymer P3) and on two controls (TCPS and $PLA_{50}$). The fluorescence values reflect the quantity of cells having proliferated on the films at 1, 2 and 3 days. The cells used are murine fibroblast lines (L929) commonly used for in vitro evaluation of medical devices.

The study shows (FIG. 2), at the various days of proliferation, a notable reduction in cell proliferation on the P4 film in comparison with the PLA$_{50}$ film and the TCPS. Indeed, the P4 film has fluorescence values significantly different from the PLA$_{50}$ and the TCPS for proliferation times of 1 and 2 days.

Cell proliferation also decreases on the P3 film, with fluorescence values significantly lower than for the TCPS at various times.

All the adhesion (FIGS. 1a-1b) and proliferation (FIG. 2) results show that the P4 film has properties that tend to decrease adhesion and cell proliferation. The anti-adhesion and antiproliferative properties of the material are due to the presence of polyethylene glycol in the composition.

C. Cytotoxicity Test

According to the EN ISO 10993-5 standard concerning the biological evaluation of medical devices, cytotoxicity can be evaluated after 24 h of incubation by a quantitative evaluation:

measurement of the cell death parameter.

Lactate dehydrogenase (LDH) is an enzyme present in eukaryotic cells which, when cell death occurs, is released in the medium. The LDH Cytotoxicity Assay Kit is a colorimetric method for assaying LDH, a cell cytotoxicity marker. LDH activity is measured by spectrophotometry at 490 nm after 24 h of incubation of human endometrial cells in the presence of the material.

The P4, P3 and PLA$_{50}$ films used are first immersed in pH 7.4 PBS for 24 h in order to swell.

Figure 3:
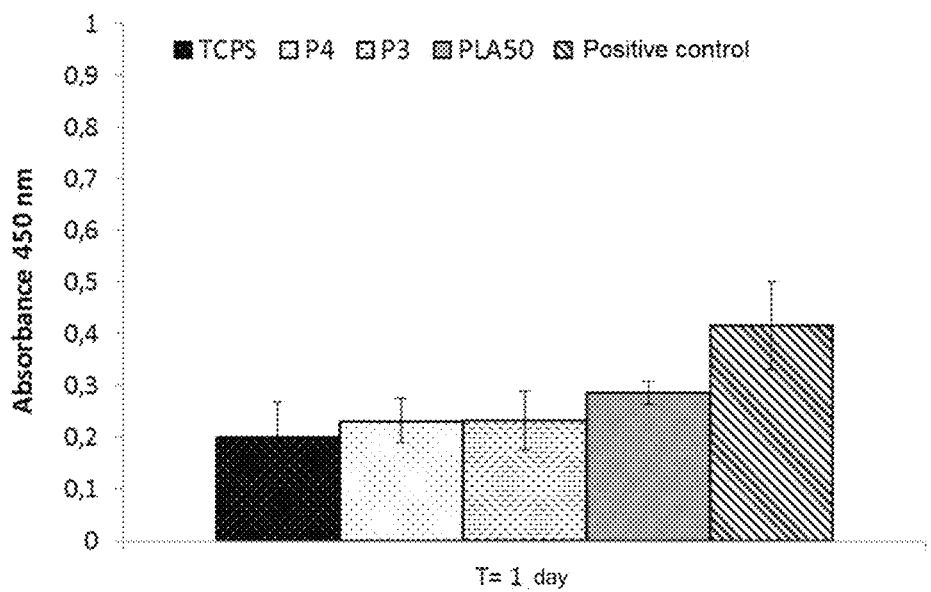
FIG. 3 shows the results obtained during a cytotoxicity test carried out on a material based on copolymer P4, a material based on copolymer P3 and on three controls (TCPS, positive control and $PLA_{50}$) in direct contact with human endometrial cells. The absorbance values at 24 hours reflect the cell lysis level: Cytotoxicity test. Copolymer P4 and copolymer P3 versus Positive control P<0.05 (Student's t-test)

As shown in FIG. 3, the P4, P3 and PLA$_{50}$ films have absorbance values between the positive control and the negative control.

Moreover, the P4 and P3 films have an absorbance value significantly different from the positive control and the P4 and P3 copolymers, the PLA$_{50}$ and the negative control are from the same population (p-value>0.05 P4–P3 versus PLA$_{50}$/Negative control). All this information supports the non-toxicity of the P4 and P3 films.

4—Evaluation of the Deployment Properties of the Anti-Adhesion Material

For all the deployment studies, the materials used are obtained from a copolymer composition P4 or a copolymer composition P3, formed by hot pressing. The films obtained from the copolymers have a thickness of 400 μm (measurement obtained with a light microscope).

A material obtained from a copolymer composition P4 formed by solvent evaporation was also prepared. The film obtained has a film thickness of 300 μm (measurement obtained with a light microscope).

All the tests are carried out in triplicate to ensure the reproducibility of the results.

A. Swelling Study

The anti-adhesion films and the PLA$_{50}$ films used in the study are cut into strips (known mass at time $t_0$) then incubated at 37° C. in saline medium (1×PBS), with shaking.

The mass of the strips is weighed at various times and the percentage of water uptake is calculated as follows:

$$\text{Water uptake } (\%) = \frac{(\text{Mass }(t) - \text{Mass }(t_0))}{(\text{Mass }(t_0))} \times 100$$

Figure 4:
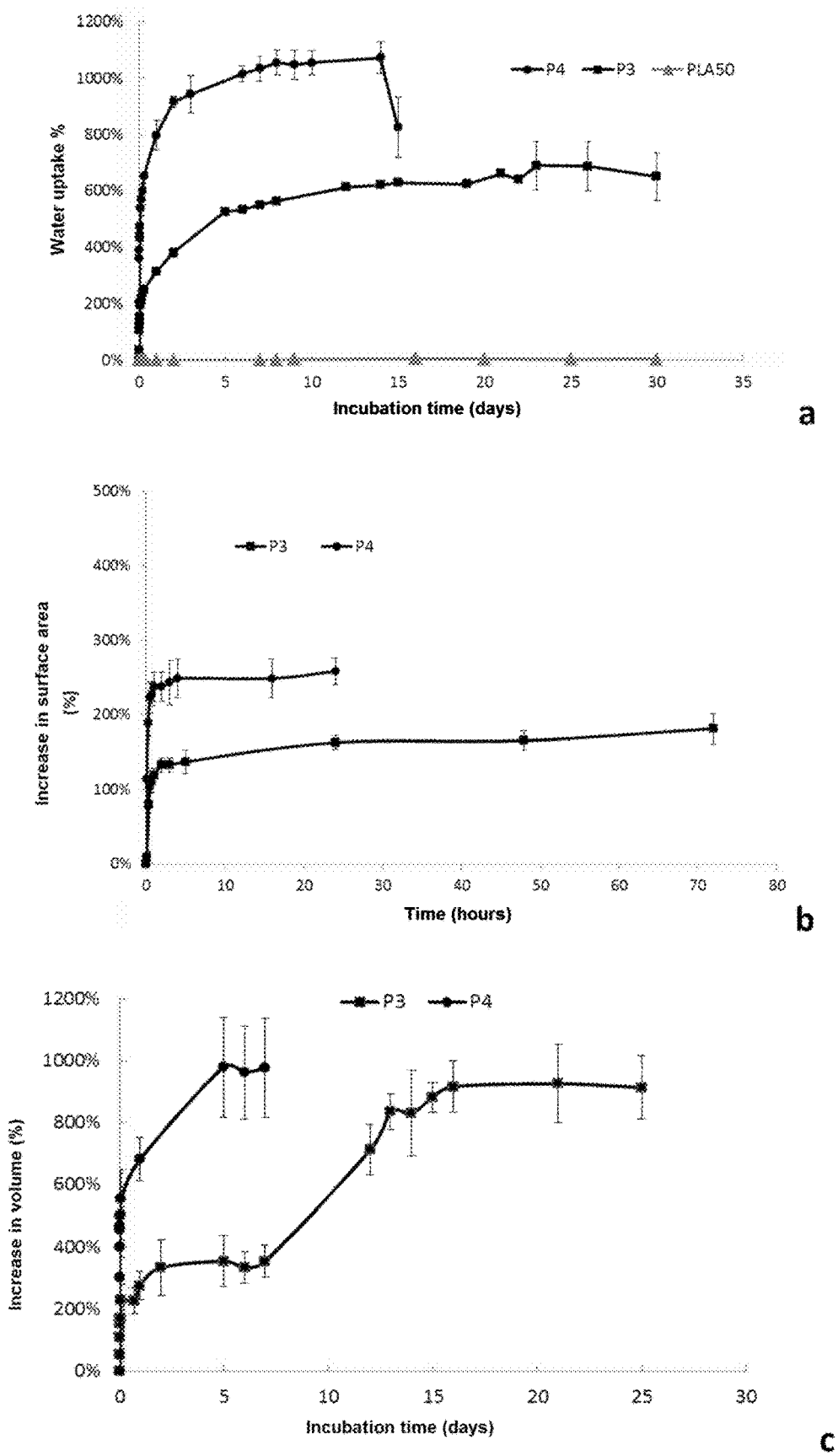
FIG. 4 (FIGS. 4a, 4b and 4c) shows the swelling properties of a material according to the invention based on copolymer P4, copolymer P3, or $PLA_{50}$ formed by hot pressing.
Figure 5:
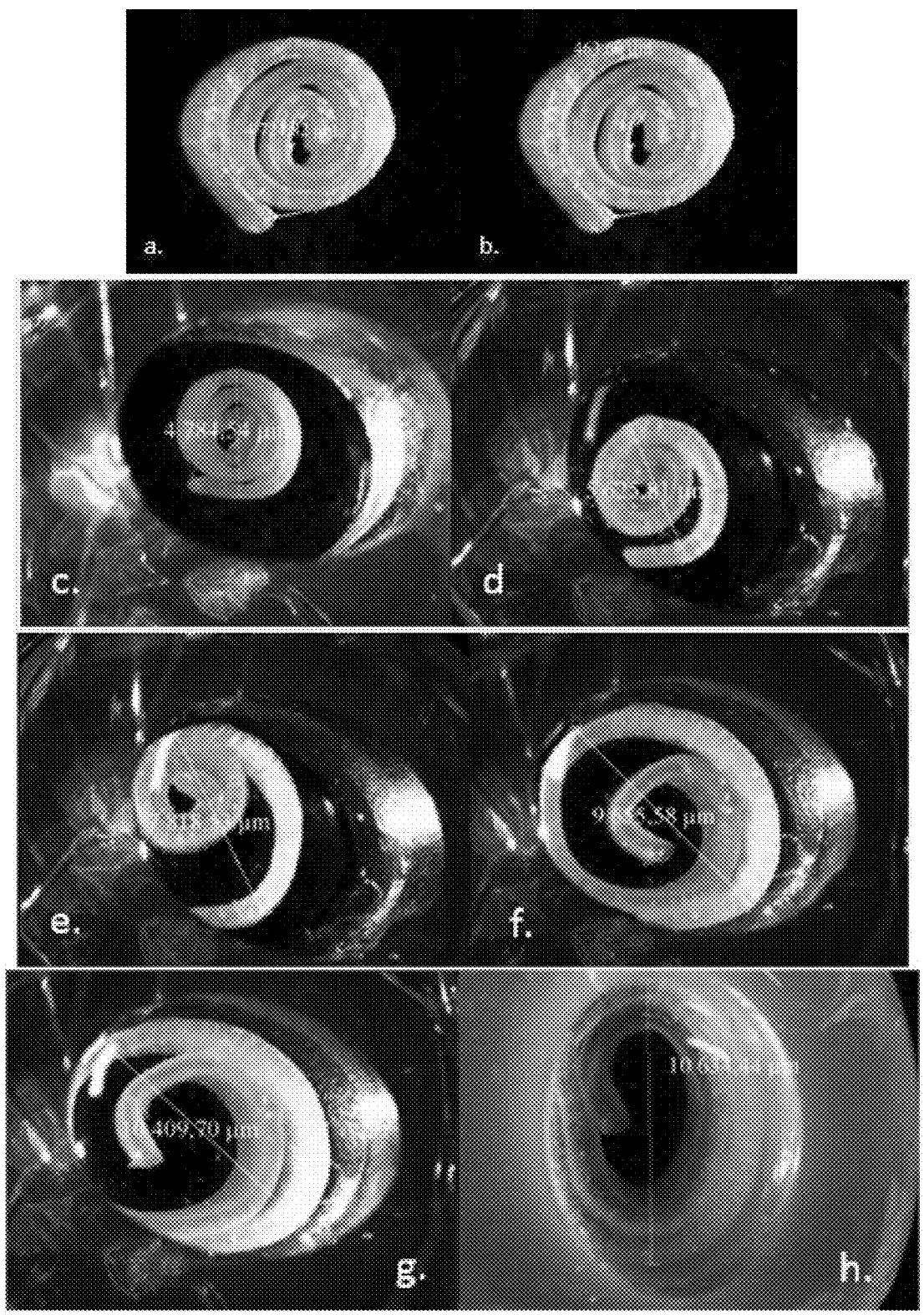
FIG. 5 shows the deployment capability of a strip of film produced from a composition according to the invention based on copolymer P4, rolled up before immersion in water (FIGS. 5a and 5b) and at various immersion times, t=2 minutes to t=24 hours (FIGS. 5c-5h). The photographs make it possible to visualize an increase in the film's length and thickness: 5a. Total diameter of the rolled-up strip (4,724 µm), 5b. Membrane thickness (463 µm). 5c. Length at t=0 (4,784 µm); 5d. Length at t=2 min (5,625 µm); 5e. Length at t=7 min (7,818 µm); 5f. Length at t=15 min (9,655 µm); 5g. Length at t=45 min (10,409 µm); 5h. Length at t=24 h (10,634 µm)

The strips of P4 film swell in PBS, with a water uptake of about 300% as of 5 minutes of incubation (FIG. 4a). The water content within the material increases over time, until reaching a percentage of about 1000%. The percentage of water uptake stabilizes from the eighth day of incubation to the fourteenth day of incubation. The P4 film then disintegrates into fragments after 15 days of incubation.

The strips of P3 film also swell in PBS, with a water uptake of about 600% as of the twelfth day of incubation, and until the twenty-second day. The copolymer P3 film then disintegrates after 25 days of immersion in PBS.

The percentage of water uptake of the P4 film obtained by solvent evaporation increases very quickly to about 900%, then stabilizes as of 24 h of incubation (not shown).

The capacity of copolymers P4 and P3 to swell in aqueous medium is due to the hydrophilic block of high molecular weight PEG. The increase in the EO/LA ratio in the copolymer composition leads to an increase in water uptake.

B. Study of Increase in Surface Area

The following study makes it possible to determine the evolution of the surface area of these same materials.

The anti-adhesion films used in the study are cut into strips (known surface area at time $t_0$) then incubated at 37° C. in saline medium (1×PBS), with shaking. The dimensions of the strips are measured at various times and the increase in surface area is determined as follows:

$$\text{Increase in surface area (\%)} = \frac{(\text{Surface area } (t) - \text{Surface area } (t_0))}{\text{Surface area } (t_0)} \times 100$$

Irrespective of the forming of the strips based on copolymer P4, they swell in PBS and double in surface area as of 5 minutes of incubation. The strips based on copolymer P3 swell in PBS and double in surface area as of 30 minutes of incubation (FIG. 4b).

Forming P4 by solvent evaporation enables an increase in surface area of about 300% as of 5 h of incubation, and the surface area of the membrane then stabilizes (not shown).

The increase in surface area differs slightly when forming P4 by hot pressing. Indeed, the surface area of the strips increases by 250% in 3 h of incubation and then stabilizes. This difference can be explained by the arrangement of the polymer chains during the forming step.

Likewise, for copolymer P3, the increase in surface area is about 150% after 5 h of incubation and the surface area then stabilizes. When one measures using a ruler the increase in surface area of a strip based on copolymer P4 formed by evaporation, the "dry" dimensions (at t=0) of which are 0.5 cm in height and 1 cm in length, a rapid increase in both dimensions is observed after only 5 minutes of incubation (t=5 minutes): height of 0.8 cm and length of 1.6 cm. At t=30 minutes, the height is 0.9 cm and the length 1.8 cm, to reach at t=24 h 1 cm in height and 2 cm in length, and stabilizes.

C. Study of Increase in Volume

The following study makes it possible to determine the evolution of the volume of the P4 and P3 films obtained by hot pressing.

The anti-adhesion films used in the study are cut into strips (known surface area at time $t_0$) then incubated at 37° C. in saline medium (1×PBS), with shaking. The dimensions of the strips are measured at various times and the increase in volume is determined as follows:

$$\text{Volume} = \text{Surface area} \times \text{Thickness}$$

$$\text{Increase in volume (\%)} = \frac{(\text{Volume } (t) - \text{Volume } (t_0))}{\text{Volume } (t_0)} \times 100$$

The volume of the copolymer P3 and copolymer P4 films increases during the time when immersed in aqueous medium (FIG. 4c). The volume of the copolymer P3 films triples as of 2 h of incubation until having a volume multiplied by a factor of 10 after 16 days of incubation. The increase in the volume of the copolymer P4 films is faster in comparison with the copolymer P3 film, with a volume multiplied by a factor of 10 as of 5 days of incubation.

D. Deployment Study

The swelling of the material formed from a copolymer composition P4 induces a deployment of the membrane in aqueous medium.

The deployment of a P4 film can be illustrated by the experiment below (FIGS. 5a-5h):

A rectangular strip of a P4 film, formed by hot pressing, 4 cm in length and 2.4 cm in width, is rolled up into a snail shape then immersed in water. The deployment of the strip and the evolution of its thickness is visualized by light microscopy.

Before its immersion in water, the thickness of the strip and its diameter once rolled up into a snail shape are measured (dry dimensions): initial thickness ($t_0$)=463 µm; initial diameter ($t_0$)=4,724 µm.

The deployment and the evolution of the thickness are monitored until t=24 h, the swelling of the copolymer stabilizing as of 24 h of incubation.

FIGS. 5a to 5h make it possible to visualize the progression of the deployment of the strip once immersed in water. The strip unrolls over time, with as of the first 2 minutes in water an increase in occupied volume (from $t_0$=4,784 µm to $t_{2\ min}$=5,625 µm). The strip deploys to fully occupy all the available space as of 15 minutes of immersion ($t_{15\ min}$=9,655 µm). The deployment phenomenon concludes with an overall length which reaches 10,634 µm at 24 h, representing more than double the initial length.

The strip deployment is the consequence of the swelling of the copolymer in water. Swelling is expressed as an increase in thickness over time, with a maximum thickness at 24 h of 1,312 µm, representing an increase of about 185% in relation to the initial thickness.

The deployment phenomenon of the strip is principally related to the capacity of the copolymer to absorb a large quantity of water. The copolymer swells and thus has the force to deploy and to occupy the available space.

5—Evaluation of Deployment and Occupation of Available Space

A film was prepared by solvent evaporation of a copolymer composition P4 and was cut into a trapezoid, to then be introduced into an IUD applicator.

Figure 6:
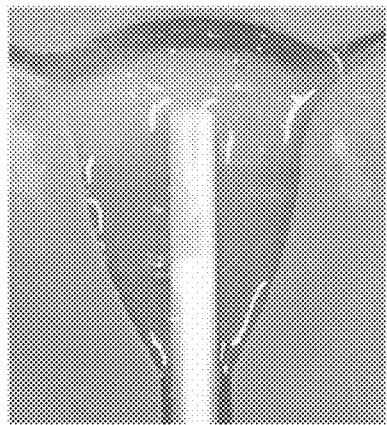
FIG. 6 is a photograph of an IUD applicator into which has been inserted a film according to the invention (P4 film), produced from a copolymer composition P4, during its insertion in a model mimicking a water-filled uterine cavity.
Figure 7:
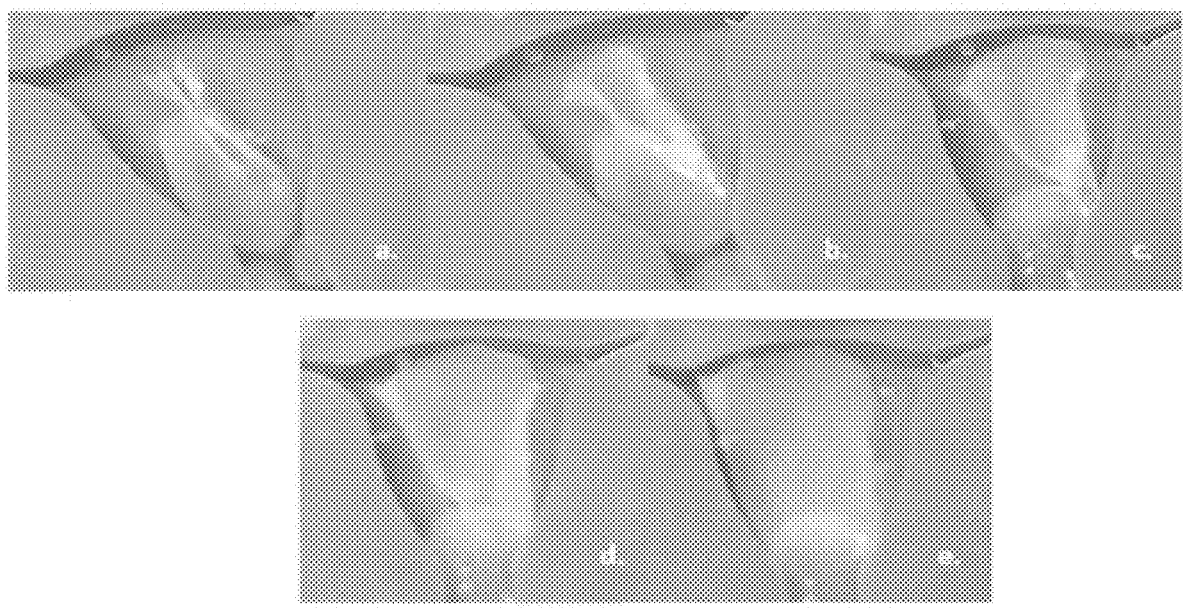
FIG. 7 shows the progressive deployment of the P4 film released in the cavity model of FIG. 6, at t=0 minute (FIG. 7a), t=1 minute (FIG. 7b), t=3 minutes (FIG. 7c), t=5 minutes (FIG. 7d) and t=8 minutes (FIG. 7e)

The trapezoidal film is expelled from the applicator in a model mimicking a water-filled uterine cavity, by means of a plunger system in order to deploy itself therein (FIG. 6). The uterine cavity model has the theoretical dimensions of a human uterine cavity.

Once the film is expelled into the cavity, it takes about 10 minutes to deploy and to cover the totality of the cavity (FIGS. 7a to 7e).

6—Evaluation of Degradation of the Anti-Adhesion Material

To determine the in vitro degradation of the anti-adhesion films formed into film by hot pressing from composition P4 or P3, a rectangle (1.5×1 cm) cut from said films is introduced in PBS, at 37° C., with mechanical shaking.

The mechanical properties of the P4 and P3 films are evaluated at various incubation times by rheological measurements.

Figure 8:
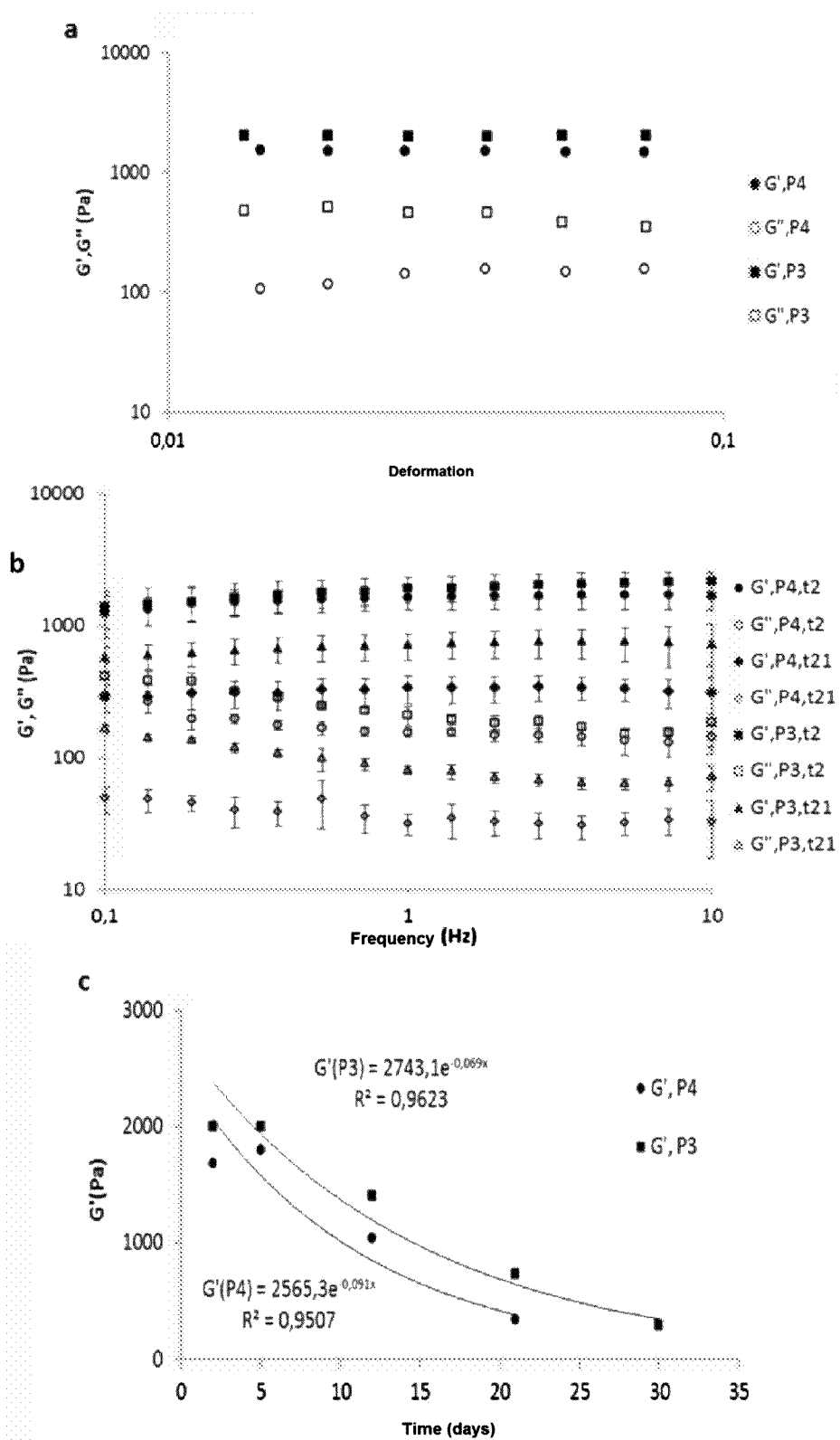
FIG. 8 shows the rheological properties of a copolymer P4 film and a copolymer P3 film when they are immersed in 37° C. PBS with mechanical shaking.

FIG. 8a shows the elastic modulus G' and the viscous modulus G" of the P3 and P4 films after 5 minutes of immersion, when a fixed-frequency (1 Hz) deformation range is applied thereto. For both copolymers, the elastic modulus is greater than the viscous modulus, characteristic of an elastic solid material.

FIG. 8b shows the variation of the elastic modulus (G') and of the viscous modulus (G") as a function of frequency (at 0.05% deformation) for the P4 and P3 films after 2 days and 21 days of immersion. For both copolymers, the modulus values decrease during the incubation period, characteristic of degradation of the copolymers. For example, for a frequency of 2 Hz, G' (P3) passes from a value of 2,005 Pa to 739 Pa after 2 days and 21 days, respectively. The loss of mechanical properties is directly related to degradation of the film.

FIG. 8c shows the elastic modulus (G') at various incubation times for the P4 and P3 films. The G' values make it possible to show first order exponential kinetics, with faster degradation kinetics for the P4 film than for the P3 film.

FIG. 8d shows the stress of the P4 film after 30 days of incubation and the stress of the P3 film after 40 days of incubation as a function of shear rate. The figure shows that the materials have a high degree of viscosity, with a critical stress ($\square_C$) of about 0.25 for P3 and 0.35 for P4.

Figure 9:
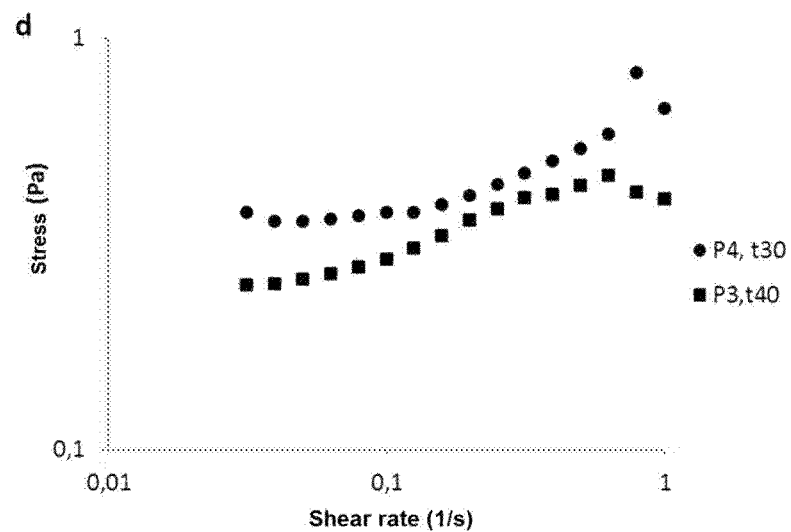
FIG. 9 shows the percentage of loss of mass of two films produced from materials according to the invention based on copolymer P4, copolymer P3 and a $PLA_{50}$ film, when they are incubated in aqueous medium. The figure shows the progressive loss of mass of the materials over time, with complete solubilization of the copolymer P3 and P4 films after 90 days of incubation.
Figure 9:
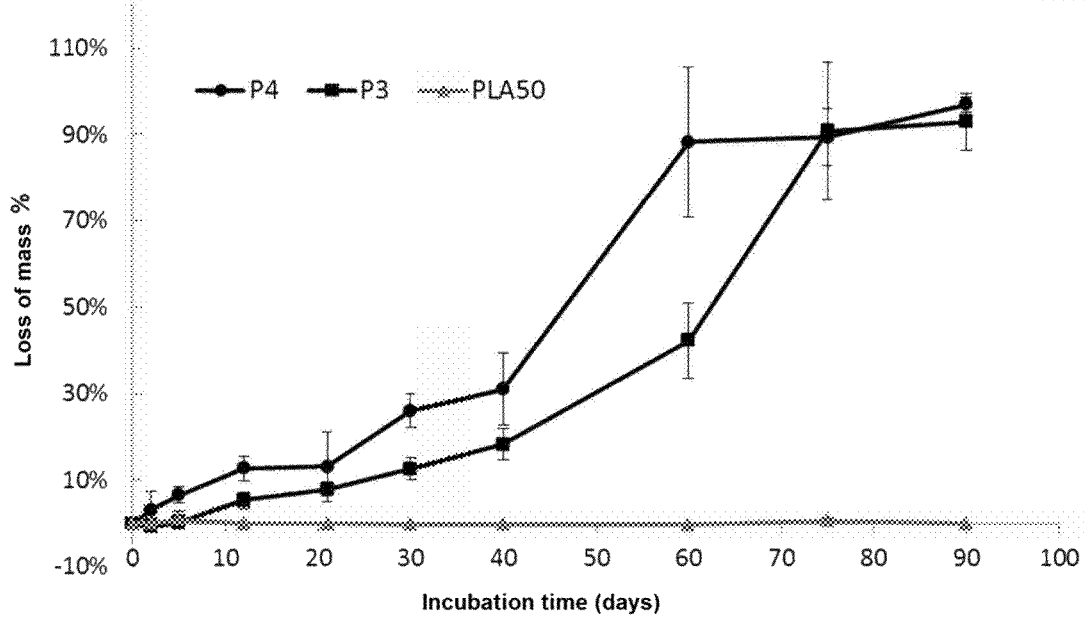

In vitro degradation is also illustrated by FIG. 9, which shows the percentage of loss of mass over time of the copolymer P3 films, the P4 films and films consisting of $PLA_{50}$. The copolymer films lose their mass until complete solubilization of the films after 90 days of incubation.

FIGS. 10a-10e illustrate the P4 film at various degradation times. It maintains its physical integrity during the first days of its immersion, namely a malleable and elastic film. The loss of its mechanical properties appears clearly after 12 days of immersion, with a film that disintegrates when handled. This observation makes it possible to show the degradation of the film. At 40 days, the film is completely fragmented.

Figure 10:
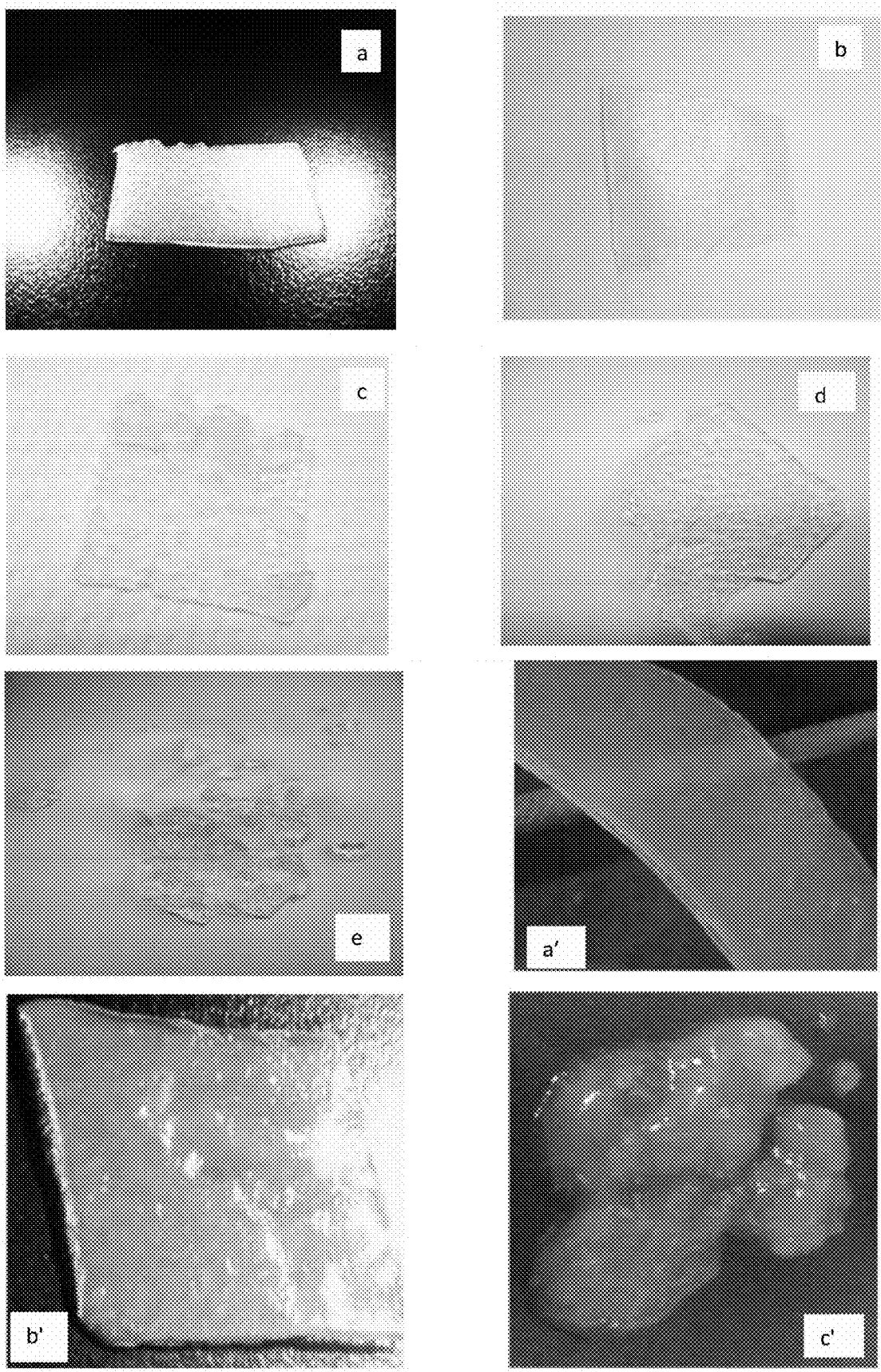
FIG. 10 shows the degradation in aqueous medium of a film produced from a material according to the invention based on copolymer P4 at various times t=24 hours (FIG. 10a), t=5 days (FIG. 10b), t=12 days (FIG. 10c), t=22 days (FIG. 10d) and t=40 days (FIG. 10e), and the degradation of a material based on copolymer P3 at t=24 hours (FIG. 10a'), t=30 days (FIG. 10b') and t=60 days (FIG. 10c'). The photographs of the films show progressive disintegration of the film, until its near-total disintegration.

FIGS. 10a' to 10c' illustrate, in turn, the film-forming properties of the P3 film (FIG. 10a') at various degradation times. The P3 film retains its mechanical properties after 30 days of immersion (FIG. 10b'), then it disintegrates into pieces of gel after 60 days of immersion (FIG. 10c').

Degradation of the copolymer is also shown by the $^1H$ NMR analysis which indicates the formation of lactic acid after 1 month and 2 weeks of incubation in PBS. The presence of lactic acid is a marker of poly(lactic acid) chain hydrolysis within the material.

Figure 11:
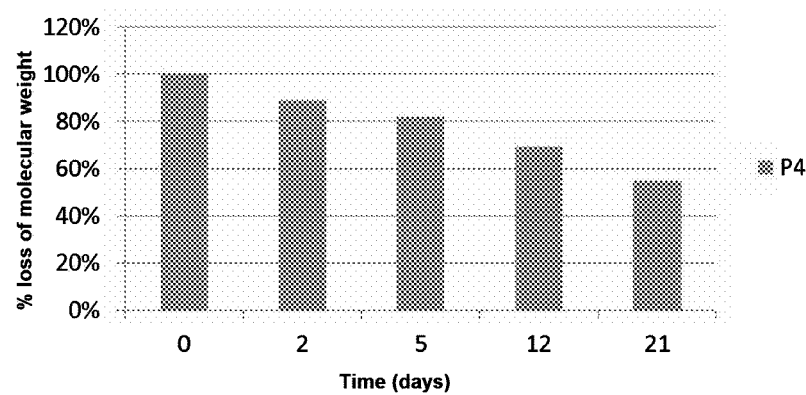
FIG. 11 shows the degradation in aqueous medium of a film produced from a material according to the invention based on copolymer P4 monitored by size-exclusion chromatography.

In vitro degradation of copolymer P4 is shown by the loss of mass (Mw) (FIG. 11) and the increase in its dispersity, obtained by size-exclusion chromatography. The Mw falls over time, with a loss of nearly 50% as of 20 days of incubation. This reduction is explained by hydrolysis of the PLA chains. Its chains of increasingly smaller molar masses are hydrolyzed to then reach the stage of oligomers then ultimately that of monomers of lactic acid.

To determine the in vivo degradation of the copolymer P4 and copolymer P3 films, rectangles (4×3.5 cm) cut from said films are introduced between the cecum and the peritoneum of a rat. A defect is made on the peritoneum and the cecum and is abraded with the compress to create adhesions between the organs, and the copolymer film is immediately applied between the abraded cecum and the peritoneal defect before the abdomen is closed. The rats are euthanatized at various times after the surgical procedure.

Figure 12:
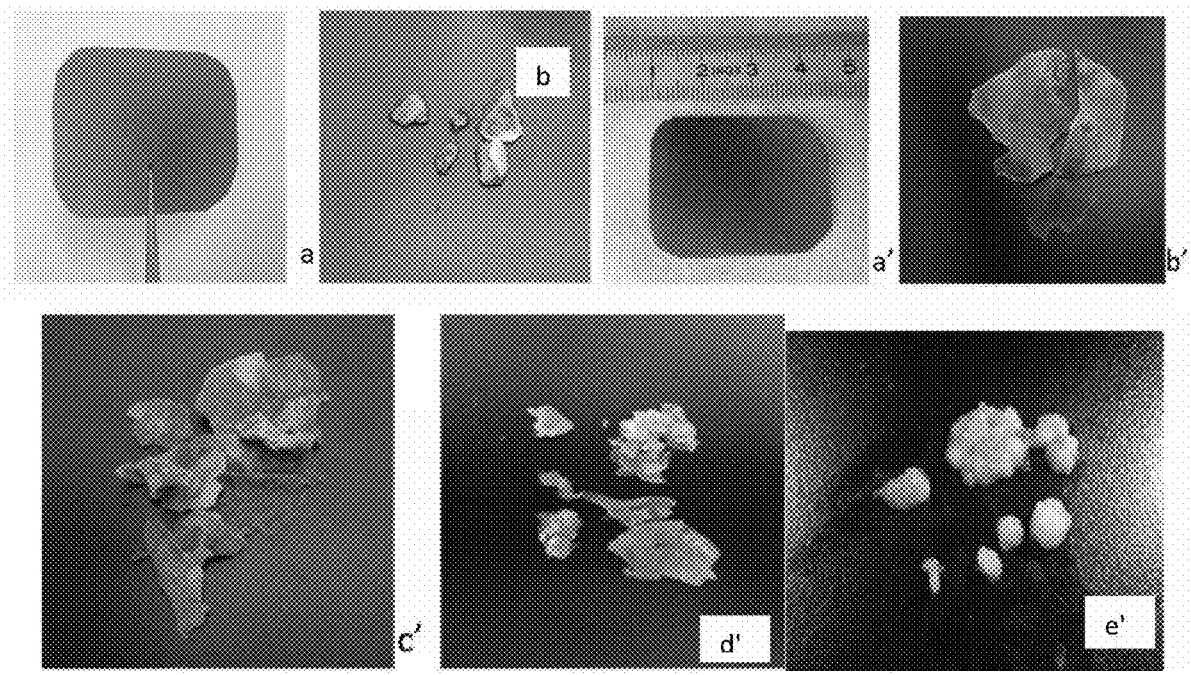
FIG. 12 shows the in vivo degradation of a film produced from a material according to the invention based on copolymer P4 at various times t=0 (FIG. 12a) and t=2 days (FIG. 12b), and the in vivo degradation of a film produced from a material according to the invention based on copolymer P3 at various times t=0 (FIG. 12a'), t=12 hours (FIG. 12b'), t=2 days (FIG. 12c'), t=5 days (FIG. 12d') and t=12 days (FIG. 12e')
Figure 13:
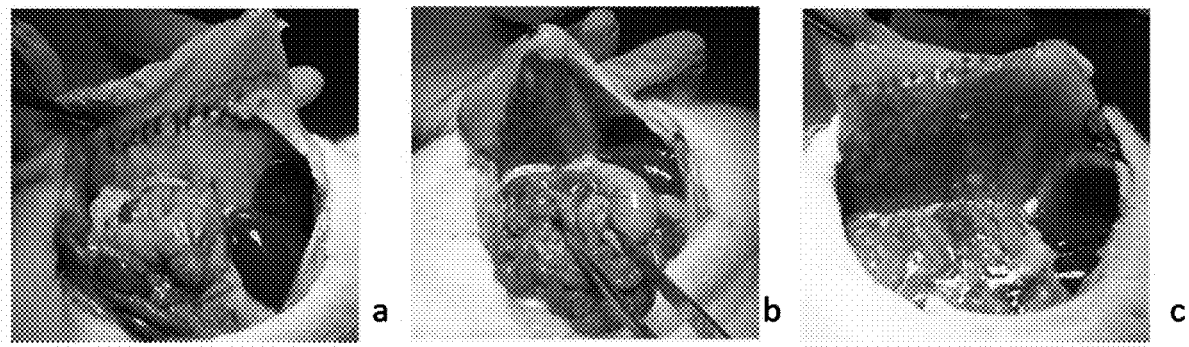
FIG. 13 shows the condition of the abdominal cavity of a rat 12 days after a peritoneal defect and an abrasion of the cecal serosa, the objective of which is to form an adhesion between the peritoneum and the cecum.

FIG. 12a shows the copolymer P4 film before its introduction into the animal (t=0), and FIG. 12b shows the copolymer P4 residues collected after 2 days of implantation. Degradation of the copolymer P4 film into gel particles is observed as of 2 days postoperative, with a large part of the initial film dissolved and eliminated from the body.

FIGS. 12b' to 12e' show the copolymer P3 film (integrated film before implantation: FIG. 12a') after various residence times in the abdominal cavity of the animal. FIG. 12b' and FIG. 12c' show the P3 film fragments collected after 12 h and 2 days of residence in the animal's body, respectively. FIG. 12d' shows the P3 film in small pieces of film after 5 days of residence and FIG. 12e' shows the P3 film in gel particles after 12 days, with the majority of the initial film dissolved and eliminated from the abdominal cavity.

7—Evaluation of the Anti-Adhesion Efficacy of Copolymers P4 and P3 on a Rat Peritoneal Adhesion Model Materials and Methods Thirty-four Wistar females are anesthetized after muscular injection of Ketamine (50 mg/kg) and xylazine (5 mg/kg). The abdomen is disinfected with Betadine and local subcutaneous anesthesia is administered before incision of the abdomen (Lidocaine 0.1%).

A 4 cm-long vertical midline incision of the abdomen is made and then the abdominal cavity is opened. The cecal serosa is abraded with the compress and a peritoneal pastille (1 cm$^2$) is made opposite thereto. The copolymer films and Seprafilm® are placed directly in the flank between the cecum and the peritoneum and 1 ml of physiological saline solution is instilled into the abdominal cavity before closing. For the Hyalobarrier®, the gel (about 1 ml) is instilled on the peritoneum and the cecum traumatized. For the control group, the abdomen is closed directly (resorbable Vicryl 3-0 Ethicon) after abrasion of the cecum and creation of the peritoneal pastille. An injection of Buprenorphine (0.02 mg/kg) is made systematically in the first 48 hours following the surgical procedure.

The efficacy study comprises 5 groups:
Group A (n=6): With copolymer P4 film
Group B (n=6): With copolymer P3 film
Group C (n=6): With Seprafilm®; Item number 4301-03
Group D (n=6): With Hyalobarrier®
Group E (n=6): Control The adhesion score is evaluated according to the extension, the severity and the degree of the adhesions as follows:
1) evaluation of the extension of the adhesions:
    0=no adhesion
    1=adhesion concerning less than 25% of the traumatized surface
    2=adhesion concerning between 25 and 50% of the traumatized surface
    3=adhesion concerning between 50 and 75% of the traumatized surface
    4=adhesion concerning between 75 and 100% of the traumatized surface
2) evaluation of the severity of the adhesions:
    0=no adhesion
    1=fine avascular adhesion
    2=opaque vascularized adhesion
    3=total adhesion of the cecum to the peritoneal wall 3) evaluation of the degree of adhesions:
   0=no adhesion
   1=adhesion separated from the tissue by gentle pulling
   2=adhesion separated from the tissue by moderate pulling
   3=adhesion requiring strong pulling to be freed or impossible to free without lesion of the organ
SCORE:/10

Three rats from each group are sacrificed at 5 days post-surgery and 3 rats are then sacrificed at 12 days for the evaluation of the adhesion score between the cecum and the peritoneum.

Four additional rats are used to evaluate the adhesion score and the behavior of the copolymers at early times: evaluation of P3 at 12 h and 2 days postoperative, and of P4 at 2 days postoperative. One rat is used to evaluate the presence/absence of adhesion at D2 postoperative.

The animals are sacrificed by ketamine anesthesia then lethal Pentobarbital injection.

Forming the copolymer films:

The copolymer films are formed by hot pressing, and stained with a purple stain to enable better visualization of the film in the abdominal cavity when the animal is sacrificed. The copolymer films have a thickness of 400 μm and are cut into 4 cm×3.5 cm (1×L) rectangles. The films are sterilized by gamma irradiation and then stored in the freezer until the day of surgery. The films do not require hydration beforehand, nor a fixing technique in the cavity.

Two days after the procedure, the control rat exhibits no adhesion. The same is true for the rats having received a P4 and P3 film. The study provides information about the formation time of cecum/peritoneum adhesions with the absence of adhesion at D2 postoperative. The P3 film is present at D2 (FIG. 11c') at the traumatized region, whereas the P4 film degrades with only small gel particles in the cavity (FIG. 11b). In the absence of adhesion in the control rat, the anti-adhesion efficacy of the copolymers at D2 cannot be determined.

Five days after the surgical procedure, 3 rats from each group are sacrificed. In the control group, the rats have severe adhesions (Table 1) which concern between 75% and 100% of the peritoneal surface (extension=4), with total adhesion of the cecum to the peritoneal wall (severity=3) and the impossibility of freeing the cecum without lesion of the organ (degree=3). After application of Seprafilm®, adhesions are observed at D5 with an average score of 7.33. In the group having received Hyalobarrier®, the score is zero. No adhesion is observed, proof of its efficacy at D5 postoperative.

In the group with the copolymer P4 film, 2 rats have adhesions, the third has an unharmed cavity. With an average score of 4.66, the adhesion score remains clearly lower than the score of the control group.

In the group with the copolymer P3 film, no adhesion is observed (score zero) and the film is in small pieces (FIG. 11d') in the cavity.

TABLE 1

Evaluation of anti-adhesion efficacy after 5 days postoperative

| | Rat | Extension | Severity | Degree | Adhesion score | Average adhesion score |
|---|---|---|---|---|---|---|
| Group A: Copolymer P4 | 1 | 4 | 3 | 1 | 8 | 4.66 |
| | 2 | 1 | 2 | 3 | 6 | |
| | 3 | 0 | 0 | 0 | 0 | |

TABLE 1-continued

Evaluation of anti-adhesion efficacy after 5 days postoperative

| | Rat | Extension | Severity | Degree | Adhesion score | Average adhesion score |
|---|---|---|---|---|---|---|
| Group B: Copolymer P3 | 7 | 0 | 0 | 0 | 0 | 0 |
| | 8 | 0 | 0 | 0 | 0 | |
| | 9 | 0 | 0 | 0 | 0 | |
| Group C: Seprafilm ® | 13 | 4 | 3 | 3 | 10 | 7.33 |
| | 14 | 1 | 2 | 2 | 5 | |
| | 15 | 3 | 2 | 2 | 7 | |
| Group D: Hyalobarrier ® | 19 | 0 | 0 | 0 | 0 | 0 |
| | 20 | 0 | 0 | 0 | 0 | |
| | 21 | 0 | 0 | 0 | 0 | |
| Group E: Control | 25 | 4 | 3 | 3 | 10 | 10 |
| | 26 | 4 | 3 | 3 | 10 | |
| | 27 | 4 | 3 | 3 | 10 | |

Twelve days after the surgical procedure, the 3 remaining rats from each group are sacrificed in turn and the adhesion score is evaluated (Table 2). The adhesion score at D12 for the control group is high (score 8.6), characteristic of vascularized adhesions covering in all the rats at least 50% of the traumatized surface.

After application of Seprafilm®, we observe adhesions at D12 with an average score of 4.3. The placing of the film is not simple, since it is extremely friable. In view of the results, the anti-adhesion efficacy is not demonstrated.

In the group having received Hyalobarrier®, 2 rats have adhesions of intensity comparable to the control group, with adhesion of the cecum with the peritoneum with the impossibility of freeing the cecum without lesion of the organ. The third rat of the group has an unharmed cavity. Thus, Hyalobarrier® plays an anti-adhesion role over the short term (D0 to D5), then the gel is degraded particularly by enzymatic hydrolysis, and does not enable a barrier role over a period of 12 days (score=6.6).

For the group with the copolymer P4 film, the adhesion score is similar to that observed at D5. The adhesion score of copolymer P4 (score=5.3) is between the adhesion score of the competing products Hyalobarrier® and Seprafilm®. Because of the early degradation of the copolymer P4 film, the film does not enable an anti-adhesion effect over the long term.

In the group with the copolymer P3 film, no adhesion is observed (score zero), and the peritoneum is healed macroscopically. Copolymer P3 is found in the form of gel particles (FIG. 11th'). The anti-adhesion efficacy of P3 is unambiguous.

TABLE 2

Evaluation of anti-adhesion efficacy after 12 days postoperative

| | Rat | Extension | Severity | Degree | Adhesion score | Average adhesion score |
|---|---|---|---|---|---|---|
| Group A: Copolymer P4 | 4 | 0 | 0 | 0 | 0 | 5.3 |
| | 5 | 2 | 3 | 3 | 8 | |
| | 6 | 2 | 3 | 3 | 8 | |
| Group B: Copolymer P3 | 10 | 0 | 0 | 0 | 0 | 0 |
| | 11 | 0 | 0 | 0 | 0 | |
| | 12 | 0 | 0 | 0 | 0 | |
| Group C: Seprafilm ® | 16 | 1 | 1 | 1 | 3 | 4.3 |
| | 17 | 4 | 3 | 3 | 10 | |
| | 18 | 0 | 0 | 0 | 0 | |
| Group D: Hyalobarrier ® | 22 | 4 | 3 | 3 | 10 | 6.6 |
| | 23 | 4 | 3 | 3 | 10 | |
| | 24 | 0 | 0 | 0 | 0 | |

TABLE 2-continued

Evaluation of anti-adhesion efficacy after 12 days postoperative

|  | Rat | Extension | Severity | Degree | Adhesion score | Average adhesion score |
|---|---|---|---|---|---|---|
| Group E: | 28 | 4 | 3 | 3 | 10 | 8.6 |
| Control | 29 | 3 | 2 | 1 | 6 |  |
|  | 30 | 4 | 3 | 3 | 10 |  |

In the control group, the surgical procedure traumatizing the abdominal cavity leads to severe adhesions between the peritoneum and the injured cecum. Postoperative application of the copolymer P4 film enables a reduction in the severity of the adhesions. Application of the copolymer

The invention claimed is:

1. A composition based on copolymers comprising AB block copolymers selected from the group consisting of ABA and BAB triblock copolymers and mixtures thereof, wherein:
   the A block is a polyester selected from the group consisting of poly(lactic acid) (PLA), poly(glycolic acid), poly-caprolactone (PCL), poly-butyrolactone (PBL), poly-hydroxyalkanoates (PHA), and copolymers thereof;
   the B block is a poly-oxyethylene (PEG);
   the molecular mass in weight of the B blocks is between 80 kDa and 125 kDa, +/−10%; and
   the ethylene oxide unit/ester unit molar ratio is between 1 and 3.

2. The composition based on copolymers according to claim 1, wherein the molecular mass in weight of the B blocks in the copolymer is between 90 and 115 kDa, +/−10%.

3. The composition based on copolymers according to claim 1, wherein the molecular mass in weight of the B blocks in the copolymer is between 100 kDa and 110 kDa, +/−10%.

4. The composition based on copolymers according to claim 1, wherein the A blocks are poly(lactic acids) selected from the group consisting of poly(L-lactic acid), poly(D-lactic acid), poly(D,L-lactic acid) and copolymers thereof.

5. The composition based on copolymers according to claim 4, wherein PLLA represents at least 50% by weight of the A blocks.

6. The composition based on copolymers according to claim 4, wherein PLLA represents from 75% to 100% by weight of the A blocks.

7. An anti-adhesion material comprising the copolymer composition according to claim 1.

8. The anti-adhesion material according to claim 7, wherein said material is formed by extrusion, solvent evaporation, hot pressing or 3D printing.

9. The anti-adhesion material according to claim 7, in the form of a film having in aqueous medium a swelling ratio of 1 to 20.

10. The anti-adhesion material according to claim 7, in the form of a film having in aqueous medium a swelling ratio at least equal to 4.

11. The anti-adhesion material according to claim 7, wherein the copolymers degrade after a residence time in aqueous medium between 2 and 20 days.

12. A Medical device for preventing intrauterine synechiae comprising the anti-adhesion material according to claim 7.

13. The Medical device according to claim 12, wherein the anti-adhesion material is in the form of a trapezoidal film intended to be deployed in the uterine cavity in order to mold to the contours and to be juxtaposed with the walls thereof.

14. The Medical device according to claim 12, comprising means for inserting the anti-adhesion material in the uterine cavity.

15. A method for preventing intrauterine synechia in a woman, comprising positioning an anti-adhesion material according to claim 7 in the uterine cavity of the woman.

16. A method for preventing intrauterine synechia in a woman according to claim 15, wherein the woman has undergone a surgical procedure in the uterine cavity.

17. The composition based on copolymers according to claim 1, wherein the molecular mass in weight of the B blocks in the copolymer is 95 kDa, +/−10%.

18. The composition based on copolymers according to claim 1, wherein the molecular mass in weight of the B blocks in the copolymer is 100 kDa, +/−10%.

* * * * *